(12) United States Patent
Tesluk et al.

(10) Patent No.: US 7,490,620 B2
(45) Date of Patent: Feb. 17, 2009

(54) FLUID CONDUIT CONNECTOR APPARATUS (75) Inventors: Christopher Tesluk, Providence, RI (US); Malcolm Bock, Medfield, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 171 days.

(21) Appl. No.: 10/784,639

(22) Filed: Feb. 23, 2004

(65) Prior Publication Data

US 2005/0184264 A1  Aug. 25, 2005

(51) Int. Cl.
*F16L 37/23* (2006.01)
*F16L 39/00* (2006.01)
*F16K 51/00* (2006.01)
*A61F 5/00* (2006.01)

(52) U.S. Cl. .......... 137/15.09; 251/149.8; 251/148; 602/13; 285/124.5; 137/614.05

(58) Field of Classification Search ... 285/124.1–124.5; 251/148, 149.8, 149.6; 602/13; 137/614.02–614.06, 137/15.01, 15.08, 15.09
See application file for complete search history.

(56) References Cited

U.S. PATENT DOCUMENTS

| 1,608,239 | A |   | 11/1926 | Rosett |   |
|---|---|---|---|---|---|
| 1,670,318 | A | * | 5/1928 | Shaff | 137/496 |
| 1,695,848 | A | * | 12/1928 | Higgins | 251/263 |
| 1,883,240 | A | * | 10/1932 | Phelan | 251/117 |
| 2,280,485 | A |   | 4/1942 | Harris | 33/1 |
| 2,628,850 | A | * | 2/1953 | Summerville | 251/149.7 |
| 2,638,915 | A | * | 5/1953 | Mitchell | 137/599.02 |
| 2,694,393 | A |   | 11/1954 | Brown | 128/38 |
| 2,694,395 | A |   | 11/1954 | Brown | 123/38 |
| 3,057,001 | A |   | 10/1962 | Rapata | 16/2 |
| 3,287,031 | A |   | 11/1966 | Simmons et al. | 285/27 |
| 3,469,863 | A | * | 9/1969 | Riester et al. | 285/124.4 |
| 3,728,875 | A |   | 4/1973 | Hartigan et al. | 66/172 E |
| 3,733,577 | A |   | 5/1973 | Hammond | 339/91 R |
| 4,013,069 | A |   | 3/1977 | Hasty | 128/24 R |
| 4,029,087 | A |   | 6/1977 | Dye et al. | 128/24 R |
| 4,030,488 | A |   | 6/1977 | Hasty | 128/24 R |
| 4,066,084 | A |   | 1/1978 | Tillander | 128/327 |
| 4,091,804 | A |   | 5/1978 | Hasty | 128/24 R |

(Continued)

FOREIGN PATENT DOCUMENTS

DE  19846922 A1  4/2000

(Continued)

OTHER PUBLICATIONS

PCT International Search Report, May 25, 2005, 4 pgs.

(Continued)

*Primary Examiner*—Stephen M Hepperle
*Assistant Examiner*—Andrew J Rost
(74) *Attorney, Agent, or Firm*—Edward S. Jarmolowicz (57) ABSTRACT

A fluid conduit connector apparatus that the approximates pneumatic characteristics of a removed pneumatic system component when a fluid conduit is removed from a pneumatic system. The fluid conduit connector apparatus includes a port portion having a valve disposed therein. The valve closes to provide a reduced fluid orifice when a fluid conduit is removed from the port. The reduced fluid orifice is configured to provides pneumatic characteristics of the device being disconnected to facilitate uninterrupted operation of a timed pressure source having pneumatic sensing capability.

10 Claims, 11 Drawing Sheets

U.S. PATENT DOCUMENTS

| | | | | |
|---|---|---|---|---|
| 4,156,425 A | 5/1979 | Arkans | ................ | 128/24 R |
| 4,198,961 A | 4/1980 | Arkans | ................ | 128/24 R |
| 4,207,875 A | 6/1980 | Arkans | ................ | 128/24 R |
| 4,207,876 A | 6/1980 | Annis | ................ | 239/24 R |
| 4,253,449 A | 3/1981 | Arkans et al. | ................ | 128/24 R |
| 4,280,485 A | 7/1981 | Arkans | ................ | 128/24 R |
| 4,355,632 A | 10/1982 | Sandman | ................ | 128/24 R |
| 4,580,816 A | 4/1986 | Campbell et al. | ................ | 285/321 |
| 4,624,248 A | 11/1986 | Poole et al. | ................ | 128/89 R |
| 4,696,289 A | 9/1987 | Gardner et al. | ................ | 128/64 |
| 4,754,993 A * | 7/1988 | Kraynick | ................ | 285/124.4 |
| 4,762,121 A | 8/1988 | Shienfeld | ................ | 128/64 |
| 4,762,504 A | 8/1988 | Michaels et al. | ................ | 439/345 |
| 4,804,208 A | 2/1989 | Dye | ................ | 285/26 |
| RE32,939 E | 6/1989 | Gardner et al. | ................ | 128/64 |
| 4,867,699 A | 9/1989 | Oda et al. | ................ | 439/355 |
| 4,872,736 A | 10/1989 | Myers et al. | ................ | 385/60 |
| 5,007,411 A | 4/1991 | Dye | ................ | 601/151 |
| 5,022,387 A | 6/1991 | Hasty | ................ | 601/152 |
| 5,031,604 A | 7/1991 | Dye | ................ | 601/152 |
| 5,041,025 A | 8/1991 | Haitmanek | ................ | 439/681 |
| 5,176,406 A | 1/1993 | Straghan | ................ | 285/24 |
| 5,186,163 A | 2/1993 | Dye | ................ | 601/27 |
| 5,217,384 A | 6/1993 | Merten et al. | ................ | 439/304 |
| 5,219,185 A | 6/1993 | Oddenino | ................ | 285/26 |
| 5,249,830 A | 10/1993 | Calmettes et al. | ................ | 285/319 |
| 5,273,254 A | 12/1993 | McNaughton et al. | ................ | 251/149.6 |
| 5,330,366 A | 7/1994 | Tsuji et al. | ................ | 439/352 |
| 5,354,260 A | 10/1994 | Cook | ................ | 602/13 |
| 5,370,423 A | 12/1994 | Guest | ................ | 285/39 |
| 5,383,894 A | 1/1995 | Dye | ................ | 606/201 |
| 5,387,110 A | 2/1995 | Kantner et al. | ................ | 439/59 |
| D357,736 S | 4/1995 | Dye | ................ | D24/129 |
| 5,435,009 A | 7/1995 | Schild et al. | ................ | 2/22 |
| 5,437,610 A | 8/1995 | Cariapa et al. | ................ | 601/152 |
| 5,443,289 A | 8/1995 | Guest | ................ | 285/39 |
| D363,988 S | 11/1995 | Dye | ................ | D24/129 |
| 5,478,119 A | 12/1995 | Dye | ................ | 285/26 |
| 5,518,416 A | 5/1996 | Kantner et al. | ................ | 439/352 |
| 5,575,762 A | 11/1996 | Peeler et al. | ................ | 601/152 |
| 5,588,954 A | 12/1996 | Ribando et al. | ................ | 601/149 |
| 5,588,955 A | 12/1996 | Johnson, Jr. et al. | ................ | 601/152 |
| 5,591,200 A | 1/1997 | Cone et al. | ................ | 606/201 |
| 5,626,556 A | 5/1997 | Tobler et al. | ................ | 601/151 |
| 5,711,757 A | 1/1998 | Bryant | ................ | 601/23 |
| 5,725,485 A | 3/1998 | Ribando et al. | ................ | 601/152 |
| 5,743,755 A | 4/1998 | Aoki | ................ | 439/354 |
| 5,795,312 A | 8/1998 | Dye | ................ | 601/151 |
| 5,843,007 A | 12/1998 | McEwen et al. | ................ | 601/152 |
| 5,876,359 A | 3/1999 | Bock et al. | ................ | 601/150 |
| 5,881,769 A * | 3/1999 | Hopson | ................ | 137/614.2 |
| 5,897,142 A | 4/1999 | Kulevsky | ................ | 285/308 |
| 5,951,502 A | 9/1999 | Peeler et al. | ................ | 601/149 |
| 5,988,704 A | 11/1999 | Ryhman | ................ | 285/307 |
| 5,989,204 A | 11/1999 | Lina | ................ | 601/152 |
| 5,997,495 A | 12/1999 | Cook et al. | ................ | 602/62 |
| 6,062,244 A | 5/2000 | Arkans | ................ | 137/1 |
| 6,105,933 A * | 8/2000 | Kanno et al. | ................ | 251/331 |
| 6,129,688 A | 10/2000 | Arkans | ................ | 601/152 |
| 6,152,495 A | 11/2000 | Hoffman et al. | ................ | 285/148.19 |
| 6,231,532 B1 | 5/2001 | Watson et al. | ................ | 601/150 |
| 6,238,230 B1 | 5/2001 | Sadler et al. | ................ | 439/350 |
| 6,257,626 B1 | 7/2001 | Campau | ................ | 285/81 |
| 6,257,627 B1 | 7/2001 | Fujiwara et al. | ................ | 285/305 |
| 6,290,662 B1 | 9/2001 | Morris et al. | ................ | 601/149 |
| 6,296,617 B1 | 10/2001 | Peeler et al. | ................ | 601/152 |
| 6,319,215 B1 | 11/2001 | Manor et al. | ................ | 601/152 |
| 6,394,131 B1 * | 5/2002 | Fross et al. | ................ | 137/614.05 |
| 6,423,053 B1 | 7/2002 | Lee | ................ | 604/533 |
| 6,436,064 B1 | 8/2002 | Kloecker | ................ | 602/13 |
| 6,440,093 B1 | 8/2002 | McEwen et al. | ................ | 601/150 |
| 6,468,237 B1 | 10/2002 | Lina | ................ | 601/150 |
| 6,494,852 B1 | 12/2002 | Barak et al. | ................ | 601/151 |
| 6,537,099 B2 | 3/2003 | Herlinger et al. | ................ | 439/352 |
| 6,544,202 B2 | 4/2003 | McEwen et al. | ................ | 601/150 |
| 6,547,284 B2 * | 4/2003 | Rose et al. | ................ | 285/124.1 |
| 6,592,534 B1 | 7/2003 | Rutt et al. | ................ | 601/151 |
| 6,629,941 B1 | 10/2003 | Ishibashi et al. | ................ | 601/152 |
| 2002/0096883 A1 | 7/2002 | Youssefifar | ................ | 285/319 |
| 2003/0045153 A1 | 3/2003 | Yamawaki | ................ | 439/352 |
| 2003/0075923 A1 | 4/2003 | Lepoutre | ................ | 285/330 |

FOREIGN PATENT DOCUMENTS

| | | |
|---|---|---|
| EP | 0552515 A1 | 7/1993 |
| EP | 0861651 A1 | 9/1998 |
| EP | 1018329 A2 | 7/2000 |
| GB | 2313784 A | 12/1997 |
| WO | WO 99/63892 | 12/1999 |
| WO | WO 2004/011842 A1 | 2/2004 |
| WO | WO 2004/011842 A1 | 5/2004 |

OTHER PUBLICATIONS

PCT International Search Report, Jun. 2, 2005, 5 pgs.
PCT International Search Report, Jun. 2, 2005, 7 pgs.
PCT Invitation to Pay Additional Fees, Jun. 10, 2005, 6 pgs.
Tyco Healthcare Kendall, SCD Response Catalog, Mar. 2000, pp. 1-2.
Tyco Healthcare Kendall, SCD Soft Sleeve Catalog, Apr. 2001, pp. 1-2.
The Kendall Company, Vascular Therapy Products Catalog, Jan. 1996, pp. 8-5-8-7.
The Kendall Company, The New SCD Compression Sleeve, Aug. 1993, pp. 1-2.
Tyco Healthcare Kendall, Prevention Gets Personal, Mar. 2001, pp. 1, 2, 4.
Kendall SCD, Sequential Compression Sleeves, Patent Information, Jan. 1993, 6 pgs.

* cited by examiner

FLUID CONDUIT CONNECTOR APPARATUS

BACKGROUND

1. Technical Field

The present disclosure generally relates to the field of fluid conduit connectors for application to multiple fluid line systems and more particularly to fluid line connectors having a valved port.

2. Description of the Related Art

Medical conditions that form clots in the blood, such as deep vein thrombosis (DVT) and peripheral edema, are a major concern to immobile medical patients. Such patients include those undergoing surgery, anesthesia, extended periods of bed rest, etc. These blood clotting conditions generally occur in the deep veins of the lower extremities and/or pelvis. These veins, such as the iliac, femoral, popiteal and tibial return deoxygenated blood to the heart. When blood circulation in these veins is retarded due to illness, injury or inactivity, there is a tendency for blood to accumulate or pool. A static pool of blood provides an ideal environment for dangerous clot formations. A major risk associated with this condition is interference with cardiovascular circulation. Most seriously, a fragment of the blood clot can break loose and migrate. A pulmonary emboli can form a potentially life-threatening blockage in a main pulmonary artery.

The conditions and resulting risks associated with patient immobility can be controlled or alleviated by applying intermittent pressure to a patient's limb to assist in blood circulation. Known devices such as one piece pads and compression boots have been employed to assist in blood circulation. See, for example, U.S. Pat. Nos. 6,290,662 and 6,494,852.

Sequential compression devices have been used, which consist of an air pump connected to a disposable wraparound pad by a series of fluid conduits such as air tubes, for example. The wraparound pad is placed around the patient's leg. Air is then forced into different parts of the wraparound pad in sequence, creating pressure around the calves and improving venous return. These known devices suffer from various drawbacks due to their bulk and cumbersome nature of use. These drawbacks cause patient discomfort, reduce compliance and can prevent mobility of the patient as recovery progresses after surgery. It would be desirable to overcome the disadvantages of such known devices with a compression apparatus that employs a fluid connector apparatus in accordance with the principles of the present disclosure.

SUMMARY

U.S. patent application Ser. No. 10/784,323, filed on Feb. 23, 2004 and entitled Compression Apparatus, the contents of which being hereby incorporated by reference herein in its entirety, discloses an exemplary sequential compression apparatus that overcomes the disadvantages and drawbacks of the prior art by reducing bulk and improving comfort and compliance to a patient. This sequential compression apparatus includes a removable portion of a compression sleeve (wraparound pad) and a valve connector that facilitates coupling of the removable portion from a pressurized fluid source.

In the sequential compression apparatus, a predetermined fluid pressure is supplied to each of a plurality of tubes to the apparatus according to a predetermined timing sequence. Fluid pressure feedback information is acquired to ensure proper operation of the apparatus. Closure of a valve in the valve connector prevents fluid leakage when the removable portion and corresponding tube is disconnected and removed.

Valve connectors heretofore known either completely open or completely close a fluid conduit. The open or closed fluid conduit has pneumatic characteristics different from those of the previously connected system components.

In an illustrative apparatus, a controller recognizes a pressure change indicating closure of the valve connector when the removable portion is removed. The controller then begins executing a second predetermined pressure timing sequence to supply pressurized fluid to the remaining portions of the apparatus. If the valve connector is not present or malfunctions when the removable portion is removed, the controller recognizes a pressure change indicating an open fluid line and can execute an error or alarm program sequence (see, for example, the controller described in U.S. patent application Ser. No. 10/784,323, filed on Feb. 23, 2004 and entitled Compression Treatment System, the entire contents of which is hereby incorporated by reference herein).

Use of such valve connectors thus disadvantageously requires a more complicated control element in the fluid supply apparatus which must be capable of executing a plurality of pressure/timing sequences in response to acquired pressure measurements. In the illustrative apparatus, switching between multiple control sequences disadvantageously requires interruption of the system and can require manual input to initiate the second pressure/timing sequence.

It would be desirable to overcome the drawbacks of heretofore known fluid line connectors by providing a coupling valve that allows a controller to continue uninterrupted operation of a single pressure timing sequence when a removable portion is disconnected from a controlled pressure system. It would be further desirable to accommodate such uninterrupted operation of a single control sequence by providing a coupling valve that approximates the pneumatic characteristics of a removable portion of controlled pressure system. It would be desirable to provide such a connector that is inexpensive to manufacture and configured for use in a prophylaxis sequential compression apparatus.

Accordingly, a fluid conduit connector apparatus is provided that facilitates uninterrupted execution of a single pressure timing sequence when a fluid conduit is removed from a pneumatic system. The fluid conduit connector apparatus overcomes the disadvantages and drawbacks of the prior art when incorporated in a prophylaxis sequential compression apparatus by reducing control system complexity, providing ease of use and minimizing interruption to patients. Desirably, the fluid conduit connector apparatus includes a port portion including a valve to achieve the advantages of the present disclosure. Most desirably, the fluid conduit connector apparatus has a valve that approximates the pneumatic characteristics of a removed pneumatic system component. The fluid conduit connector apparatus is easily and efficiently fabricated.

The fluid conduit connector apparatus, in accordance with the principles of the present disclosure, is adapted for use with a compression apparatus. The fluid connector apparatus includes a connector having a plurality of fluid ports formed therewith that facilitates fluid communication between a plurality of fluid conduits of the compression apparatus and a pressurized fluid source. Each of the plurality of fluid ports defines a fluid orifice configured for fluid flow. A valve is disposed with one of the fluid ports. The valve is operable to engage the fluid port such that disconnect of a fluid conduit of the compression apparatus corresponding to the fluid port from the connector reduces a dimension of the fluid orifice of the fluid port.

The fluid connector apparatus can include a first connector having a first plurality of fluid ports formed therewith that fluidly communicates with a first plurality of fluid conduits. In an illustrative embodiment, the first plurality of fluid conduits is a set of three air tubes. A valve is supported with the first connector and is movable such that upon disconnection of one of the first plurality of fluid conduits from the first connector, the valve engages a corresponding fluid port in a configuration that creates a reduced fluid orifice therein. The valve is adapted to approximate pneumatic characteristics of a connected apparatus when the connected apparatus is disconnected from the first connector.

In another embodiment, one of the fluid ports includes a coupling port and one of the first plurality fluid conduits includes a quick-disconnect fitting adapted for removable mating with the coupling port. The valve is disposed in the coupling port and can, for example, include a spring loaded plunger. An illustrative coupling fitting includes an engagement portion extending therefrom. The spring loaded plunger is displaced by the engagement portion when the coupling fitting is mated to the coupling port.

In one embodiment, the coupling port includes a cap portion disposed therein. The spring loaded plunger engages the cap portion to create an orifice that provides a pneumatic behavior approximating one of the first plurality of fluid conduits when the coupling fitting is disconnected from the coupling port.

In an illustrative embodiment, the fluid connector apparatus according the present disclosure also includes a second connector in fluid communication with a second plurality of fluid conduits. In an exemplary embodiment, the second plurality of fluid conduits is a set of three air tubes. A plurality of couplings is in fluid communication with the air tubes. The first connector includes a sleeve defining a cavity adapted for mating with the plurality of couplings. The cavity defines a female mating receptacle. The plurality of couplings defines a male mating plug adapted for mating with the female mating receptacle.

In certain embodiments, the first and/or second connectors include improved streamlining of their outer surfaces to prevent snagging of the connectors on patient garments and bedding. In one embodiment, the first connector includes an interference key in the cavity to prevent the first connector from mating with legacy connector components. The second connector includes a clearance space for the interference key.

In yet another embodiment, the first plurality of fluid conduits is a set of webbed tubing having increased webbing volume between at least one pair of adjacent conduits. At least one interference rib is formed between at least one pair of adjacent fluid ports in the first plurality of fluid ports. The increased webbing volume is aligned with the interference rib if the plurality of fluid conduits is improperly oriented with said first connector. The interference rib thereby prevents attachment of improperly oriented fluid conduits to the first connector. Similarly, the second plurality of fluid conduits can include an increased webbing volume configured to interfere with an interference rib between adjacent ports in the second connector to prevent attachment of improperly oriented fluid conduits to the second connector.

In one embodiment of the present disclosure, the fluid conduit connector apparatus further includes a gasket disposed in the cavity. The gasket is adapted to provide fluid sealing between the first and second connectors when the first and second connectors are mated together.

In at least one embodiment, the sleeve includes a window extending at least partially therethrough. The second connector includes a locking arm extending therefrom. The locking arm is adapted to engage the window to releasably retain the first connector with the second connector. The sleeve can include a slot extending to the window which partially bifurcates the sleeve to define opposing snap arms for engaging the locking arm. One of the first or second connectors can include an alignment slot and the other of the first or second connectors can include an alignment rib configured for engaging the alignment slot.

In a particular illustrative embodiment, the locking arm includes a leading surface inclined at a first angle to provide a predetermined engagement force between the locking arm and snap arms, and a trailing surface inclined at a second angle to provide a predetermined disengagement force between the locking arm and snap arms. The predetermined engagement force can be designed, for example, to be less than the predetermined disengagement force.

In another embodiment of the present disclosure, a fluid connector apparatus includes a first connector having tubular walls defining a plurality of fluid ports adapted to connect to a first plurality of fluid conduits. At least one of the fluid ports comprises a coupling port. At least one of the first plurality of fluid conduits includes a coupling fitting adapted for removable mating with the coupling port. A valve is disposed within the coupling port. The valve engages the coupling port to create an orifice approximating pneumatic behavior of one of the first plurality of conduits when the coupling fitting is disconnected from said coupling port. A second connector is adapted to connect to a second plurality of fluid conduits and mate with the first connector.

In an exemplary embodiment, the valve includes a spring loaded plunger disposed in the coupling port. In one embodiment, the coupling fitting includes an engagement portion extending therefrom. The spring loaded plunger is displaced by the engagement portion when the coupling fitting is mated to said coupling port. The coupling port includes a cap portion disposed therein. The spring loaded plunger engages the cap portion to create an orifice that provides a pneumatic behavior approximating said one of the first plurality of fluid conduits when the coupling fitting is disconnected from the coupling port.

In another embodiment of the fluid connector apparatus, the second connector comprises a plurality of couplings in fluid communication with the second plurality of fluid conduits. The first connector includes a sleeve formed therewith defining a cavity adapted for mating with the plurality of couplings. The sleeve includes a window extending at least partially therethrough. The second connector includes a locking arm extending therefrom which is adapted to engage the window to releasably retain the first connector with the second connector. The sleeve includes a slot extending to the window and partially bifurcating the sleeve to define opposing snap arms for engaging the locking arm.

A particular embodiment of the present disclosure a fluid connector apparatus includes a sleeve connector having tubular walls defining a plurality of fluid ports adapted to connect to a first tubing set including an ankle tube, a calf tube and a thigh tube. One of the ports includes a coupling port. The thigh tube has a coupling fitting adapted for removable mating with the coupling port.

In the particular embodiment, a valve is disposed within the coupling port. The valve includes a spring loaded plunger which engages the coupling port to create an orifice approximating pneumatic behavior of the thigh tube when the fitting is disconnected from the coupling port. The coupling fitting includes an engagement portion extending therefrom. The spring loaded plunger is displaced by the engagement portion when the coupling fitting is mated to the coupling port. The coupling port includes a cap portion disposed therein. The spring loaded plunger engages the cap portion to create an orifice that provides pneumatic behavior approximating the thigh tube when the coupling fitting is disconnected from the coupling port.

A tubing set connector can be adapted to connect to a second tubing set and mate with the sleeve connector. The tubing set connector includes a plurality of couplings in fluid communication with the second tubing set. The sleeve connector includes a sleeve formed therewith defining a cavity adapted for mating with the plurality of couplings, and having a gasket disposed in the cavity. The gasket is adapted to provide fluid sealing between the sleeve connector and the tubing set connector. In at least one embodiment, the gasket includes a retention portion extending therefrom. The sleeve includes a gasket retention groove adapted to accept the retention portion and thereby retain the gasket to the sleeve.

In a particular embodiment, the sleeve includes a window extending at least partially therethrough. The tubing set connector includes a locking arm extending therefrom. The locking arm is adapted to engage the window to releasably retain the sleeve connector with the tubing set connector. The sleeve includes a slot extending to the window and partially bifurcating the sleeve to define opposing snap arms for engaging the locking arm. One of the sleeve connector or the tubing set connector includes an alignment slot and the other of the sleeve connector or the tubing set connector includes an alignment rib configured for engaging the alignment slot.

In another embodiment, the present application discloses a coupling apparatus including a coupling fitting permanently mounted to a first end of a fluid conduit. A second end of the fluid conduit is connected to an inflatable device. A coupling port is adapted for mating with the coupling fitting and includes a valve supported with the coupling port. The valve approximates pneumatic characteristics of the inflatable device and fluid conduit when the coupling fitting is disconnected from the coupling port.

In another particular embodiment, the coupling fitting can include a proximal cylinder and a distal cylinder extending therefrom. A central longitudinal axis extends through the proximal cylinder and distal cylinder. The proximal cylinder has an inside diameter approximately equal to the outside diameter of said fluid conduit to facilitate an interference fit therebetween. The distal cylinder has an inside diameter approximately equal to the outside diameter of said coupling port to facilitate a slip fit therebetween and includes a locking tab extending radially from the outer surface of the distal cylinder.

The coupling port includes a fluid communication channel and is incorporated with a sleeve having a detent for engaging the locking tab to removably secure the coupling fitting to the coupling port. Alternatively, the sleeve or interior surface of the first connector can include a detent cavity extending at least partially into the interior surface and adapted for accepting the locking tab. An exemplary detent cavity includes a longitudinal track portion adapted for guiding the locking tab during engagement and disengagement and an annular portion adapted for retaining the locking tab when the coupling fitting is rotated about its longitudinal axis. Along its length, the detent cavity can have varying depth or width into the interior surface. The varying depth of the detent cavity provides a predetermined engagement/disengagement force/displacement profile between the locking tab and the detent cavity. In one embodiment, the locking tab has an outer portion with an enlarged manual engagement surface to assist manipulation of the locking tab.

In an illustrative embodiment, the valve includes a spring loaded plunger. The spring is compressed by engagement between the coupling fitting and the plunger to open the coupling port for fluid communication when the coupling fitting is connected to the coupling port. The spring is extended to force the plunger into the channel. The plunger is perforated to provide a predetermined fluid resistance through the channel when the coupling fitting is disconnected from the coupling port.

In another embodiment, the present disclosure provides a fluid connector apparatus including a first connector having a first plurality of fluid ports formed therewith which fluidly communicate with a first plurality of fluid conduits. A second connector is in fluid communication with a second plurality of fluid conduits and includes a plurality of couplings in fluid communication therewith. Restrictor means within the first connector are provided for approximating pneumatic characteristics of one of the fluid conduits when it is disconnected from the first connector.

In yet another embodiment, the present disclosure provides a method of coupling a pressure source to a pneumatic device. According to the method of the present disclosure, a first plurality of fluid conduits from the pneumatic device is connected to a second plurality of conduits from the pressure source using a multi-port tube connector. One of the first plurality of conduits is disconnected from the multi-port tube connector. A valve is thereby released in the connector which approximates the pneumatic characteristics of one of the first plurality of conduits.

Another illustrative embodiment of the present disclosure provides a fluid conduit coupling. The fluid conduit coupling has a coupling fitting with a proximal cylinder and a distal cylinder monolithically formed with the proximal cylinder along a central longitudinal axis. The proximal cylinder has an inside diameter adapted for receiving a fluid conduit. The fluid conduit coupling also includes a fluid port having a male cylindrical portion extending proximally therefrom and a fluid channel extending through the port from the male cylindrical portion to a distal opening. The distal cylinder of the coupling fitting includes a female orifice adapted for mating with the male cylindrical portion of the coupling port. A valve disposed in the port is operatively configured to approximate pneumatic characteristics of a disconnected device when the coupling fitting is detached from the coupling port.

The coupling fitting of the fluid conduit coupling according to the illustrative embodiment has an engagement portion adapted to displace the valve in the coupling port. The valve includes plunger biased proximally by a spring force. The engagement portion is aligned to displace the plunger distally against said spring force when the fitting is attached to the port. The plunger providing an increased fluid passage when displaced distally and a reduced fluid passage when biased proximally.

BRIEF DESCRIPTION OF THE DRAWINGS

The objects and features of the present disclosure, which are believed to be novel, are set forth with the particularity in the appended claims. The present disclosure, both as to its organization and manner of operation, together with further objectives and advantages, may be best understood by reference to the following description, taken in connection with the accompanying drawings, which are described below.

DETAILED DESCRIPTION OF EXEMPLARY EMBODIMENTS

The exemplary embodiments of the fluid conduit connector apparatus and methods of operation disclosed are discussed in terms of prophylaxis compression apparatus and vascular therapy including a prophylaxis compression apparatus for application to a limb of a body and more particularly in terms of a compression apparatus having removable portions. It is envisioned that the present disclosure, however, finds application with a wide variety of pneumatic systems having removable fluid conduits, such as, for example, medical and industrial applications requiring timed sequences of compressed air in a plurality of air tubes.

In the discussion that follows, the term "proximal" refers to a portion of a structure that is closer to a torso of a subject and the term "distal" refers to a portion that is further from the torso. As used herein the term "subject" refers to a patient undergoing vascular therapy using the prophylaxis sequential compression apparatus. According to the present disclosure, the term "practitioner" refers to an individual administering the prophylaxis sequential compression apparatus and may include support personnel.

The following discussion includes a description of the fluid conduit connector apparatus, followed by a description of an exemplary method of operating the fluid conduit connector apparatus in accordance with the principals of the present disclosure. Reference will now be made in detail to the exemplary embodiments and disclosure, which are illustrated with the accompanying figures.

Figure 1:
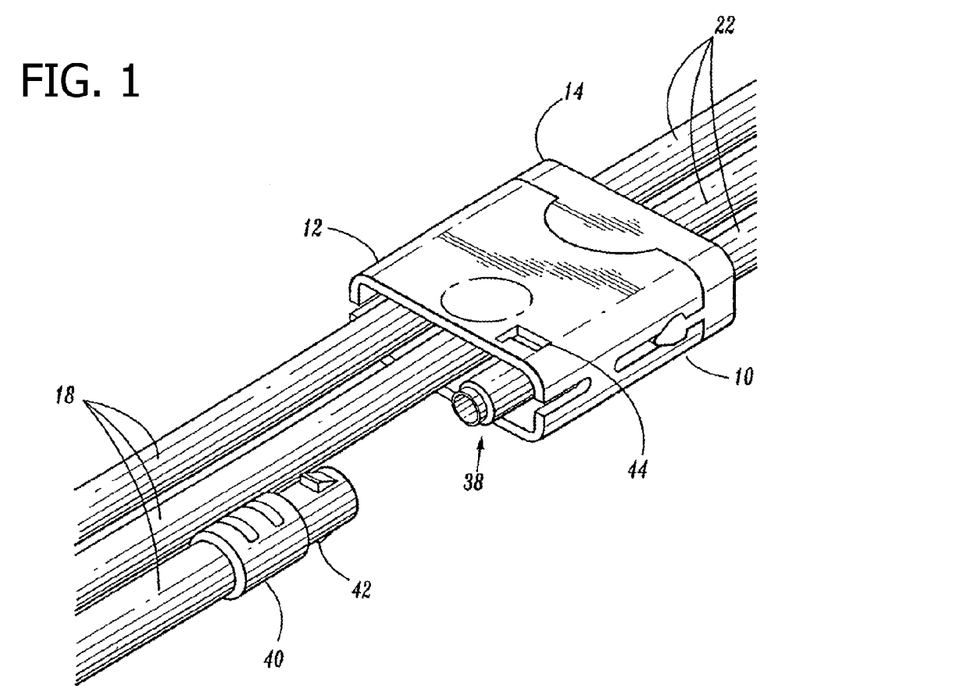
FIG. 1 is a perspective view of an illustrative embodiment of a fluid conduit connector apparatus in accordance with the principles of the present disclosure.
Figure 2:
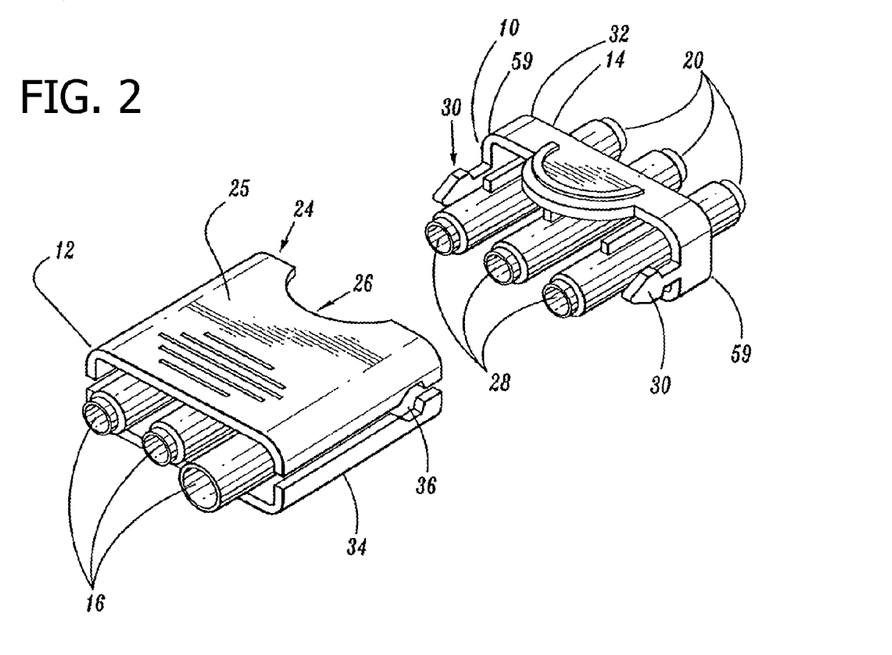
FIG. 2 is a perspective view of a first and second connector according to an illustrative embodiment of the fluid conduit connector apparatus of the present disclosure.
Figure 3:
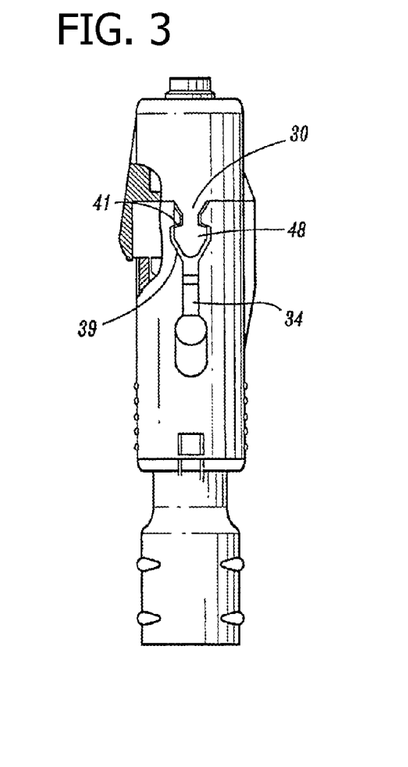
FIG. 3 is a side partial cross-sectional view of the illustrative fluid conduit connector apparatus shown in FIG. 1.
Figure 4:
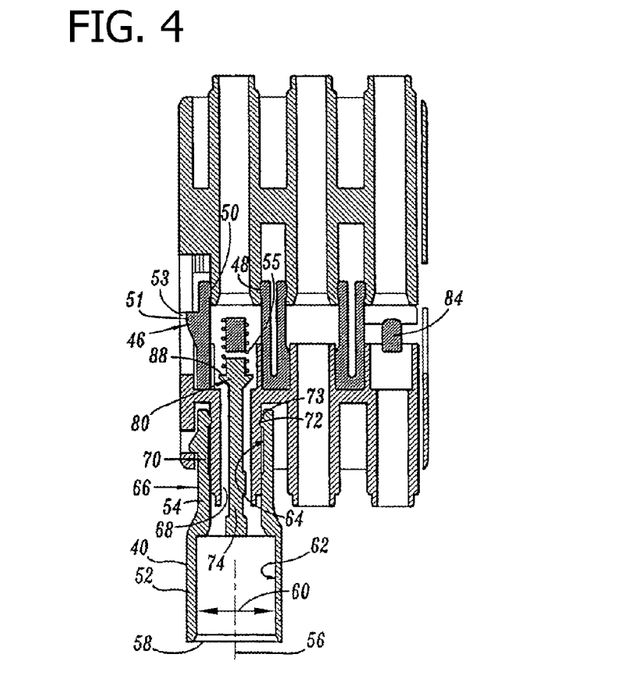
FIG. 4 is a top cross sectional view of the illustrative fluid conduit connector apparatus shown in FIG. 1.
Figure 5:
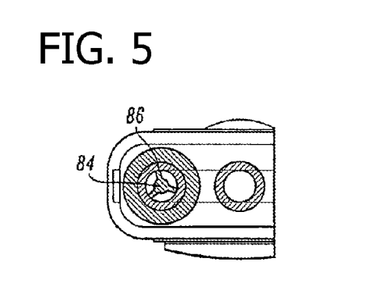
FIG. 5 is front cross sectional view of the coupling port in an illustrative fluid conduit connector apparatus according to the present disclosure.

Turning now to the figures, wherein like components are designated by like reference numerals throughout the several views. Referring initially to FIGS. 1 and 2, there is illustrated a fluid conduit connector apparatus 10, constructed in accordance with the principals of the present disclosure. The fluid conduit connector apparatus 10 includes a connector having a first connector 12 and second connector 14. First connector 12 is configured for removable engagement with a second connector 14.

Figure 15:
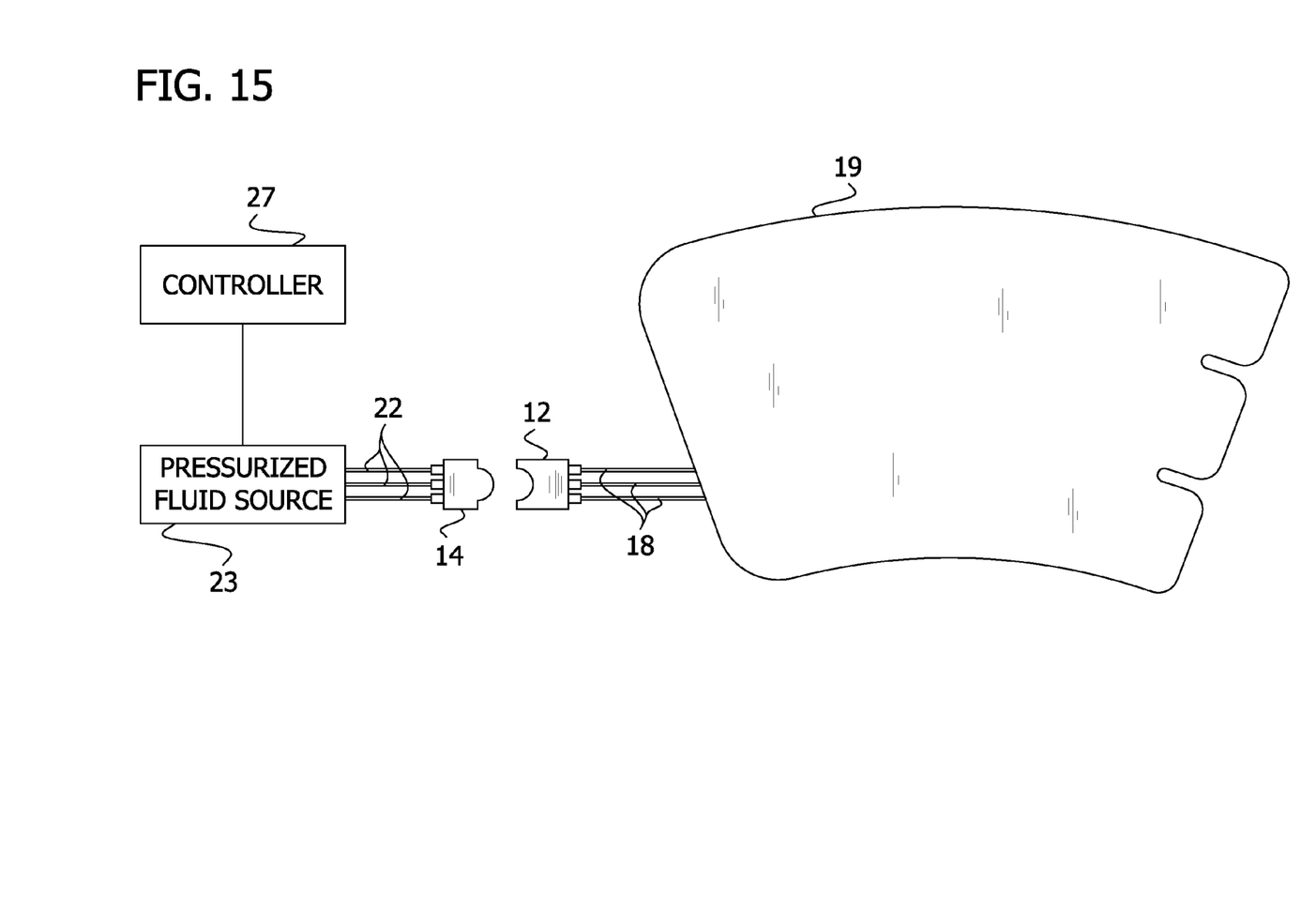
FIG. 15 is a diagrammatic view of a controller and fluid pressure source used with the fluid conduit connector apparatus.

The first connector 12 includes a first plurality of fluid ports 16 extending proximally therefrom and adapted for receiving a first plurality of fluid conduits 18. Fluid conduits 18 are connected to a compression apparatus, including for example, a compression sleeve 19 (see FIG. 15) adapted for disposal and treatment about a limb of a subject (not shown). The second connector 14 includes a second plurality of fluid ports 20 extending distally therefrom and adapted for receiving a second plurality of fluid conduits 22. Fluid conduits 22 fluidly communicate with a pressurized fluid source 23 that is adapted to inflate the compression sleeve via the advantageous configuration of fluid conduit connector apparatus 10, as described in accordance with the principles of the present disclosure. The pressurized fluid source 23 is controlled by a controller 25 that includes instructions providing a timed sequence of the pressurized fluid to the compression sleeve 19. It is envisioned that conduits 18, 22 may include various tubing such as, for example, non-webbed tubing, etc.

The fluid ports 16, 20 of connectors 12, 14 respectively, each define an inner fluid orifice or passageway that facilitate fluid communication between connectors 12, 14. In turn, connectors 12, 14 facilitate fluid communication between the pressurized fluid source and the compression sleeve. Although the fluid conduit connector apparatus 10 is illustrated as having a set of three fluid ports in each connector for connecting sets of three fluid conduits, it is contemplated that each connector can have any number of fluid ports without departing from the scope of the present disclosure.

The first connector 12 includes a sleeve 24 defining a cavity 26 having a distal opening. The cavity 26 houses distal portions of the first plurality of fluid ports 16 which extend distally within the cavity 26. The second connector 14 includes a plurality of fluid couplings 28 extending proximally therefrom. The plurality of fluid couplings 28 is formed by proximal portions of the second plurality of fluid ports 20 for alignment with the distal portions of the first plurality of fluid ports 16. A locking arm 30 extends proximally from the body portion 32 of the second connector 14. A slot 34 in the sleeve 24 of first connector 12 includes a window 36 adapted for removably accepting the locking arm 30 to retain the first connector 12 to the second connector 14.

At least one of the first plurality of ports is a coupling port 38 adapted for receiving a coupling fitting 40. The coupling fitting 40 is permanently attached to the distal end of a corresponding one of the first plurality of fluid conduits 18. A locking tab extending radially from the coupling fitting 40 is configured for engaging a detent cavity 44 in the first connector 12, for example in the sleeve 24 as shown in FIG. 1. A streamlined outer surface 25 prevents the connectors from snagging on patient clothing or bedding.

Referring now to FIGS. 3-7, the various components of the fluid conduit connector apparatus will be described in further detail.

A gasket 46 conforms to the space between the plurality of couplings 28 and the distal portion of the first plurality of fluid ports 16 within the cavity 26 when the first 12 is engaged with the second connector 14. The gasket 46 provides sealing for pressurized fluid communication between corresponding fluid conduits by providing a sealed fluid channel including the first plurality of fluid ports and second plurality of fluid ports. It is envisioned that the gasket 46 can be efficiently and inexpensively manufactured using a variety of common materials or fabrication methods, for example by injection molding an elastomeric material or dye cutting a cork or paper based gasket material. It is envisioned that the gasket 46 can be configured for retention to one or the other of the first connector 12 and second connector 14. In the illustrative embodiment, the gasket includes a proximal lip 48 configured to engage the distal portion of each of the first plurality of fluid ports to provide fluid sealing between the first connector 12 and the second connector 14. The gasket includes a retention portion extending therefrom. The sleeve 24 includes a gasket retention groove adapted to accept the retention portion and thereby retain the gasket to the sleeve 24 when the second connector 14 is removed therefrom.

The slot 34 at least partially bifurcates the sleeve 24 to allow spreading of the sleeve 24 under stress when the locking arm 30 is pressed into the slot 34 at its distal end as the first connector 12 is mated to the second connector 14. When an engagement portion 48 of the locking arm 30 reaches the window portion 36 of the slot 34 the sleeve returns to its relaxed shape to releasably retain the second connector 14 by its locking arms 30. The locking arm 48 is formed with a leading surface 39 inclined at an angle (i.e., first angle) and a trailing surface 41 inclined at a second angle. In the illustrative embodiment, the leading surface 39 is inclined at a shallower angle than the trailing 41 surface so that the force to connect the first connector 12 to the second connector 14 is lighter than the force to disconnect the first connector 12 from the second connector 14. Predetermined connection/disconnection forces can thereby be achieved by proper selection of the first and second angle when designing a particular locking arm 48.

Figure 8:
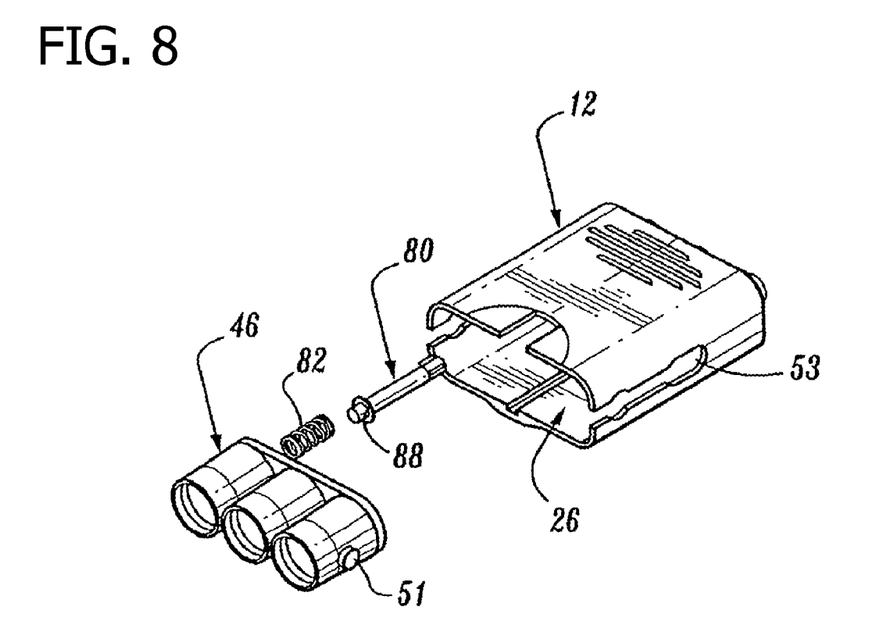
FIG. 8 is an exploded view of the various components of an illustrative first connector in a fluid conduit connector apparatus according to the present disclosure.
Figure 8A:
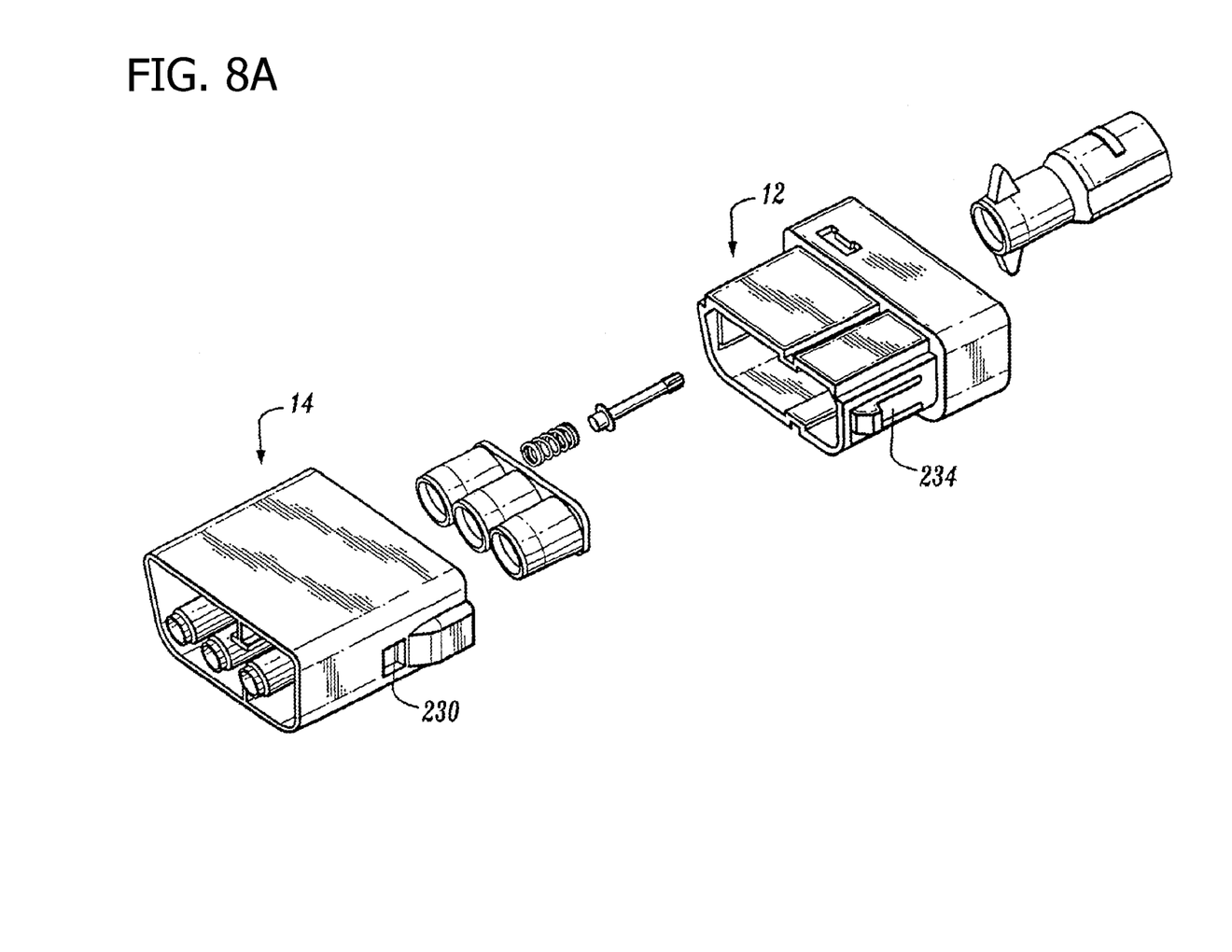
FIG. 8A is a perspective view of an alternate embodiment of the first connector shown in FIG. 8.
Figure 8B:
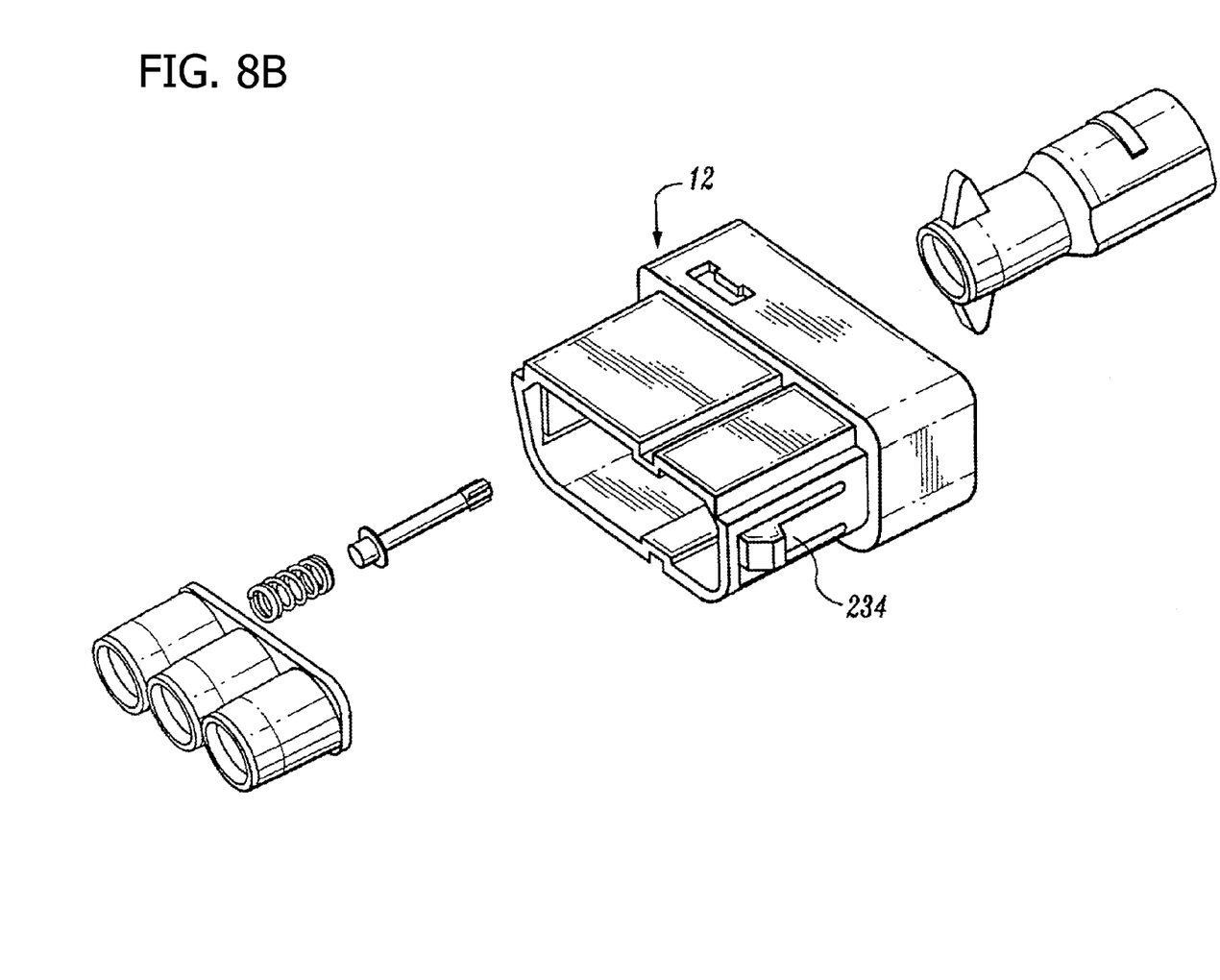
FIG. 8B is a perspective view of the first connector shown in FIG. 8A and an alternate embodiment of the second connector shown in FIG. 2.
Figure 8C:
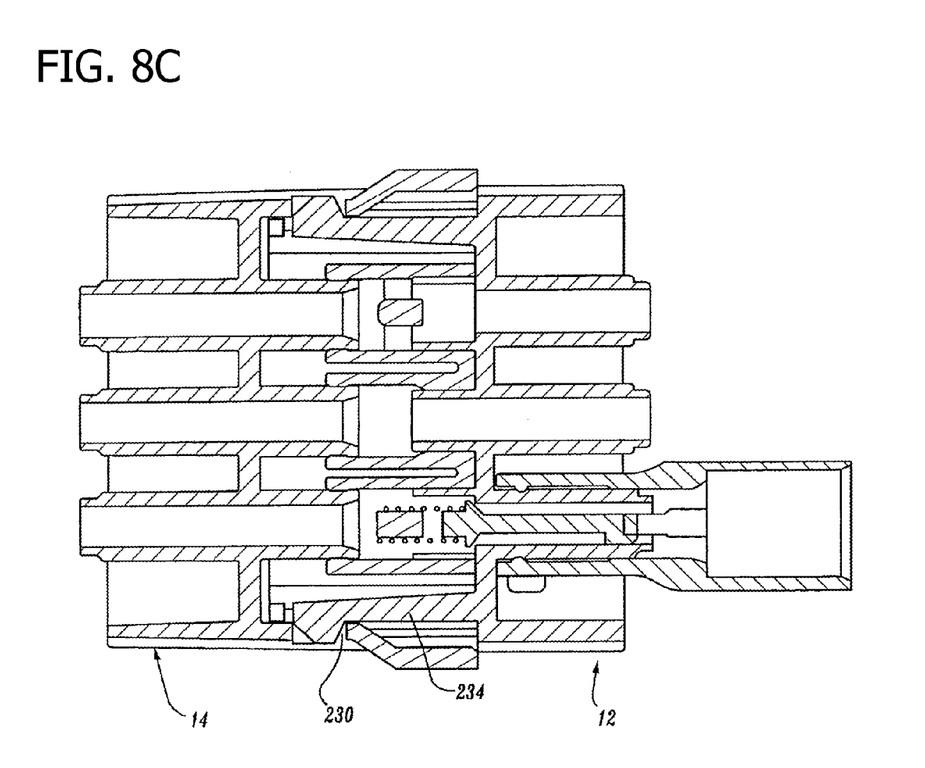
FIG. 8C is a cross-sectional plan view of the first connector and the second connector shown in FIG. 8B.

Although the illustrative embodiment described herein refers to a particular locking arm and slot configuration, it is envisioned that virtually any type of removable retention method may be used to removably retain the first connector to the second connector without departing from the scope of the present disclosure. For example, an interference fit may be provided between the first connector 12 and second connector 14 or may be provided by a properly configured deformable gasket 46. Alternatively, a snap or detent arrangement known in the art may be used to retain the first connector 12 to the second connector 14. For example, as shown in FIGS. 8A, 8B and 8C, first connector 12 includes a locking arm 234 that is configured for mating engagement with corresponding slot 230 formed in second connector 14, similar to the arm and slot structure described.

An alignment rib 59 (FIG. 1) extends radially from at least one of the plurality of couplings 28 along its longitudinal axis. A corresponding alignment slot (not shown) is provided in the inner surface of the sleeve 24 extending to the distal end thereof for accepting the alignment rib 59. It is contemplated that virtually any type of alignment rib/slot configuration commonly used in the art of for alignment of mating connectors can be used without departing from the scope of the present disclosure.

The coupling fitting 40 includes a proximal cylinder 52 and a distal cylinder 54 aligned along a longitudinal axis 56. The proximal cylinder 52 includes a proximal opening 58 and an inside diameter 60 defining an inner surface 62 configured for a press fit corresponding to the outside diameter of one of the first plurality of fluid conduits 18. In the illustrative embodiment, the corresponding fluid conduit is an air tube which is press fit into the proximal cylinder 52 through its proximal opening 58. In an illustrative embodiment, the fluid conduit is substantially permanently attached to the proximal cylinder 52 by friction. In alternative embodiments a variety of suitable adhesives may be applied to the inner surface 62 of the proximal cylinder 52 to permanently attach the fluid conduit and provide a fluid tight seal therebetween. For example, it is envisioned that a silicon adhesive, rubber cement, a material specific adhesive compound, an o-ring, a gasket or the like can be used according to methods well known in the art to attach the fluid conduit to the coupling fitting.

The distal cylinder 54 comprises an inner surface defined by an inside contour 64 revolved about the longitudinal axis 56 and an outer surface 66 defined by an outside diameter. In the illustrative embodiment, the inside contour 64 includes a sealing portion 68, a flexing portion 70 and an annular lip portion 72. The sealing portion 68 has an inside diameter adapted for a tight fit against the outside surface of the coupling port 38 to provide at least partial fluid sealing therebetween. The annular lip portion 72 defines an annular ring that compresses against the outside surface of coupling port 38 and provides fluid sealing therebetween. The flexing portion 70 is defined by a reduced wall thickness which allows the distal cylinder 54 to deflect inwardly to facilitate engagement of the locking tab 42 to the detent cavity 44.

Although the illustrative embodiment is described with respect to a particular retention and sealing configuration between the coupling fitting 40 and coupling port 38, it is envisioned that virtually any type of coupling fitting retention and sealing method known in the art can be used between the coupling fitting 40 and the external surface of the coupling port 38 without departing from the scope of the present disclosure. For example, it is envisioned that a threaded collar, a cantilever snap arm or the like can be used for attachment of the coupling fitting 40 to the coupling port 38 or to the first connector 12.

Figure 9:
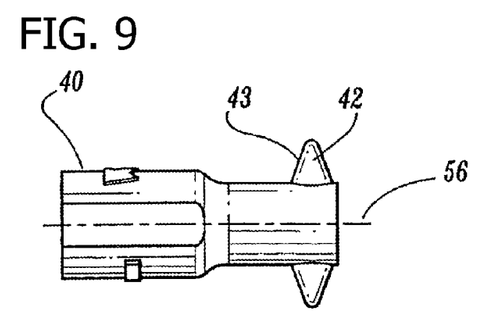
FIG. 9 is a side view of an illustrative coupling fitting according to the present disclosure.
Figure 10:
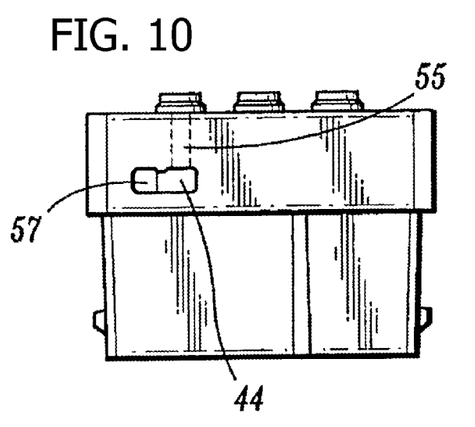
FIG. 10 is a top view of a first or second connector including a detent cavity according to an illustrative embodiment of the present disclosure.

In another example referring to FIGS. 9 and 10, the sleeve 24 or interior surface of the first connector 12 can include a detent cavity 44 extending at least partially into the interior surface and adapted for accepting the locking tab 42 of the coupling fitting 40. A detent 57 of tab 42 is inserted into sleeve 24 to become disposed in cavity 44. Detent 57 is rotated through cavity 44, via manipulation of fitting 40 and retained in position by bump formed in the wall of cavity 44. In an alternate embodiment, the detent cavity shown in FIG. 10 includes a longitudinal track portion 55 (shown in phantom) adapted for guiding the locking tab 42 (FIG. 9) during engagement and disengagement and an annular portion 57 adapted for retaining the locking tab 42 (FIG. 9) when the coupling fitting 40 is rotated about its longitudinal axis 56. Along its length, the detent cavity 44 can have varying depth or width into the interior surface. The varying depth of the detent cavity 44 provides a predetermined engagement/disengagement force/displacement profile between the locking tab 42 and the detent cavity. In one embodiment, the locking tab has an outer portion with an enlarged manual engagement surface 43 to assist manipulation of the locking tab 42.

In an illustrative embodiment of the invention, the coupling fitting includes an engagement portion 74 adapted for opening a valve 76 disposed within the coupling port 38. The engagement portion 74 extends distally from a transverse wall 78 within the coupling fitting 40 to displace a plunger 80 in the valve 76. In the illustrative embodiment, the transverse wall 78 is disposed within the coupling fitting 40 about between the proximal cylinder 52 and the distal cylinder 54 and orthogonal to the longitudinal axis 56. At least one fluid passageway extends through the transverse wall.

Although the illustrative embodiment is described in terms of a distally extending engagement portion, it is envisioned that virtually any type of valve engagement structure can be used to displace a valve plunger 80 within the scope of the present disclosure. For example, a flat surface of the transverse wall 78 or a rib extending from the inner surface of the distal cylinder 54, can be aligned with a complementary structure within a valve 76 to displace a valve plunger 80 when the coupling fitting 40 is engaged with the coupling port 38.

The illustrative embodiment includes a valve 76 is disposed within the coupling port 38. The valve 76 includes a plunger 80 movable along the longitudinal axis of the coupling port 38 and biased proximally by a spring 82. The spring 82 is supported by the gasket 46 which is held in place in cavity 26 by protrusion 51 on the gasket 46. Adhesive may alternatively be used to maintain gasket 46 in position. The gasket 46 includes a spring seat formed along the longitudinal axis of any gasket passageway to be aligned with a coupling port. (FIGS. 4-5) The spring seat in the illustrative embodiment includes a central stub 84 supported by radial spars 86 within the gasket opening.

Figure 7:
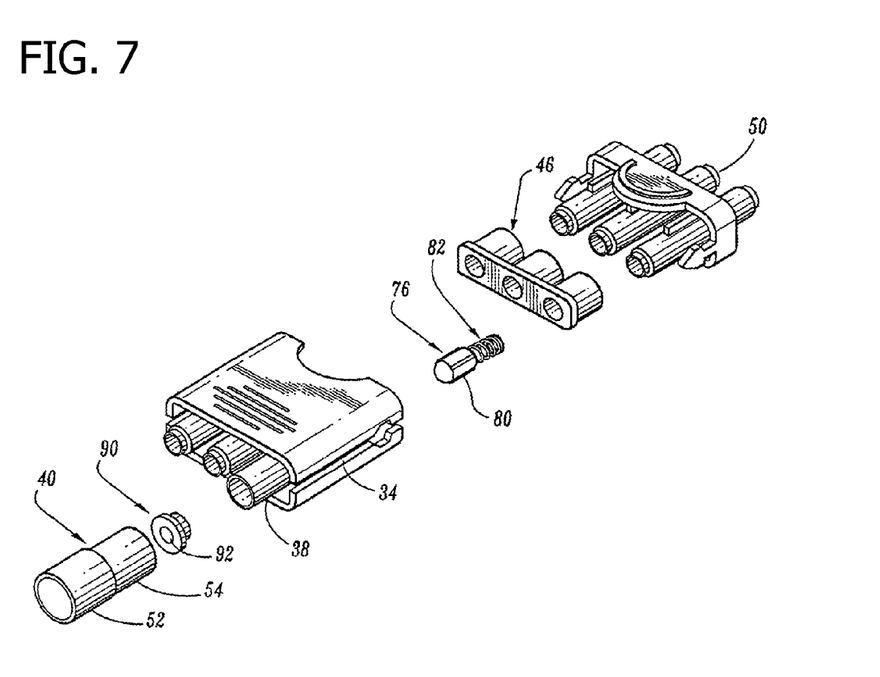
FIG. 7 is an exploded view of the various components of an illustrative fluid conduit connector apparatus according to the present disclosure.

The valve can be easily assembled by installing the spring 82 over the distal end of the plunger 80 to form a plunger and spring sub-assembly. The plunger 80 includes a step 88 to engage the proximal end of the spring 82. The plunger and spring sub-assembly can then be installed into the coupling port 38 from its proximal end. The gasket 46 can then be installed into the cavity 26. Alternatively, the plunger and spring sub-assembly can be installed to the gasket 46 by fitting the spring 82 to the spring seat before installing the gasket 46 spring 82 and plunger 80 together to the first connector 12. FIGS. 7 and 8 provide two illustrative embodiments of a plunger 80 according to the present disclosure.

Although the present disclosure illustrates the use of a coil spring 82 to bias the plunger 80, it is contemplated that virtually any type of plunger and spring arrangement known in the art can be used to provide biasing of the plunger 80 within the scope of the present disclosure. For example, it is envisioned that spring force could be applied to the plunger 80 by forming a plastic cantilever spring arm that could be formed within the first connector 12. Alternatively a structure similar to the spring seat could be formed of elastomeric material as part of the gasket 46 to provide a biasing force to the plunger 80 without departing from the scope of the present disclosure.

When the coupling fitting 40 is engaged with the coupling port 38, the engagement portion 74 of the coupling fitting forces the plunger 80 to move distally against the force of the spring 82 which is thereby compressed. An open fluid connection is thereby provided from the fluid conduit connected to the coupling fitting 40, through the coupling port 38 to the corresponding one of the second plurality of fluid conduits 22, i.e., the corresponding air tube.

For example, a portion of the compression sleeve that fluidly communicates with the pressurized fluid source via coupling port 38 may be removed from the remainder of the compression sleeve. The remaining portion of the compression sleeve continues to provide treatment to the limb of the subject. Upon removal of the selected portion, the coupling fitting 40 is disconnected and not engaged to the coupling port 38. Spring 82 forces the plunger 80 to its proximal limit of travel where the plunger 80 engages a proximal stop such that valve 76 is in a closed position.

The plunger 80 is configured to cooperate with an internal structure in the coupling port 38 to define a reduced fluid orifice when the plunger 80 is displaced to its proximal limit. The reduced fluid orifice is designed to provide pneumatic characteristics approximating the pneumatic characteristics of a detached device.

In an illustrative embodiment, (FIGS. 6-7), a cap 90 having a fluid passageway 92 therethrough is disposed in the proximal opening of the coupling port 38. The cap 90 provides a stop defining a proximal limit of plunger travel and is configured to cooperate with the plunger 80 of valve 76, such that valve 76 reduces the dimension of the fluid orifice of coupling port 38.

Figure 6:
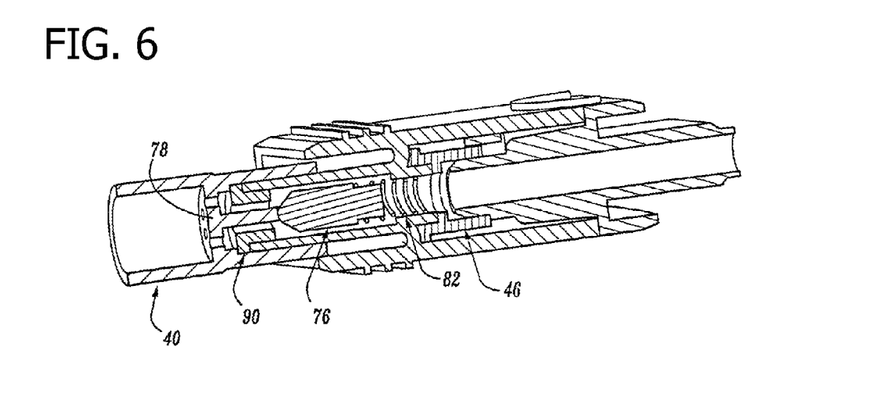
FIG. 6 is a side cross sectional perspective view of the fluid conduit connector apparatus according to an illustrative embodiment of the present disclosure.
Figure 6A:
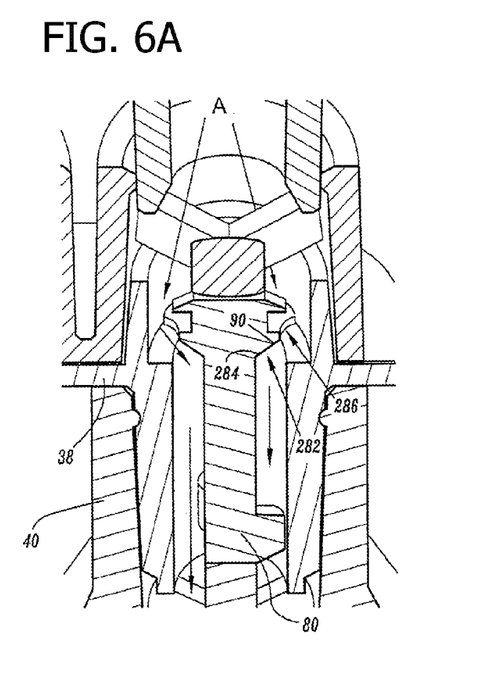
FIG. 6A is a cutaway perspective view of the fluid conduit connector apparatus shown in FIG. 6.
Figure 6B:
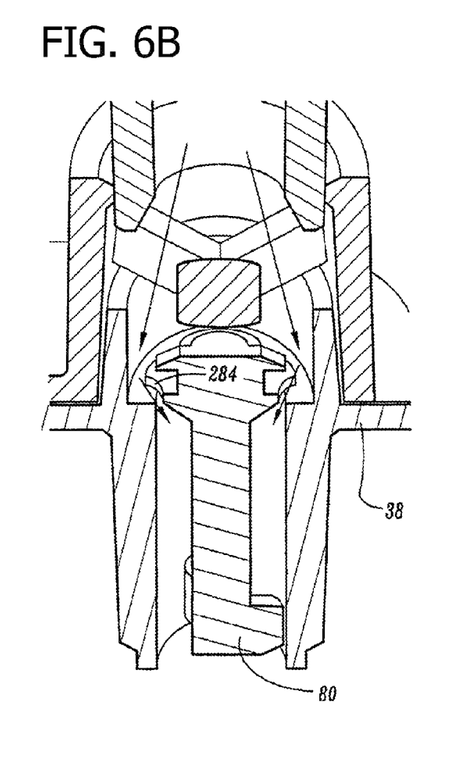
FIG. 6B is a cutaway perspective view of the fluid conduit connector apparatus shown in FIG. 6.

For example, as shown in FIGS. 6A and 6B, coupling fitting 40 is connected to the coupling port 38 to force plunger 80 distally and open the fluid connection (FIG. 6A), described above, for inflating a removable portion of an inflatable compression sleeve (not shown). To provide such an open connection, a valve seat 282 of plunger 80 is disposed via spring 82 (not shown in FIGS. 6A and 6B for clarity), out of engagement with a conical seat 284 of cap 90. This configuration allows air to flow around the conical seat 284 and through conduit 22 (not shown), and out to the inflatable removable portion of the compression sleeve, as shown by arrows A.

For removal of the removable portion of the compression sleeve, coupling fitting 40 is removed from coupling port 38. Spring 82 forces valve seat 282 into engagement with a counter bore edge of conical seat 284. Thus, this configuration advantageously reduces the dimension of the fluid orifice of coupling port 38 such that air only flows through cavities defined by semi-circular slots 286 of valve seat 282 and the bore edge of conical seat 284. Slots 286 are formed on the sides of valve seat 282. The cavities defined by slots 286 and conical seat 284 facilitate fluid flow that approximates the pneumatic behavior of the removable portion of the compression sleeve when coupling fitting 40 is connected to coupling port 38 during an open fluid connection. The cavities defined by slots 286 and conical seat 284 may have various configurations and dimensions including geometries such as, for example, elliptical, polygonal, etc.

This configuration advantageously approximates the pneumatic characteristics of a detached device. It is contemplated that the fluid orifice of coupling port 38 may be variously configured such that corresponding engagement with plunger 80 reduces the orifice dimension to approximate fluid flow through coupling port 38 that would otherwise occur with valve 76 in the open position. It is further contemplated that plunger 80 may includes openings to approximate fluid flow. It is envisioned that valve 76 is operable to reduce the dimension of the fluid orifice of coupling port 38 over a range of closed positions, including partial fluid flow, leakage, etc. to approximate fluid in the port or alternatively, the orifice may completely close to prevent fluid flow through the corresponding port. In a completely closed configuration, pump speed or other settings may be adjusted.

In a particular embodiment, the present disclosure provides an air tubing connector for use with a compression apparatus having removable portions, see, for example, the compression sleeve described in U.S. patent application Ser. No. 10/784,323, filed on Feb. 23, 2004 and entitled Compression Apparatus. Three separate air tube are connected to an ankle portion, a calf portion and a knee portion of the apparatus. Each portion is supplied with a timed sequence of compressed air through its respective air tube. The proximal end of each of the three air tubes is connected to the first plurality of fluid ports 16 in a first connector 12 according to the present disclosure. A mating set of three air tubes extends from a timed pressure source and is connected to the second plurality of fluid ports 18 in a second connector 14 according to the present disclosure.

In the illustrative embodiment, the distal end of the thigh tube is connected to the first connector 12 via a coupling fitting 40 and port 38 as described hereinbefore. When a patient no longer requires the thigh portion of the prophylaxis compression apparatus, the thigh portion can be removed and the tubing attached thereto can be disconnected from the first connector at the coupling port 38. Operation of the valve 76 in the coupling port 38 provides a reduced fluid orifice that restricts airflow therethrough to approximate the pneumatic characteristics of the thigh portion and its corresponding air tube. Thus, sensors in the timed pressure source will not detect a change in fluid pressure or flow rate when the thigh portion is removed. This allows the timed pressure source to continue supplying uninterrupted timed air pressure to the ankle and calf portions of the prophylaxis compression apparatus.

Figure 11:
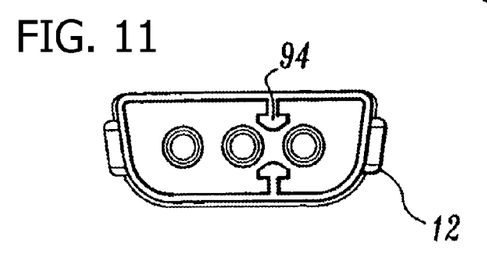
FIG. 11 is a front view of a first or second connector including an interference rib according to an illustrative embodiment of the present disclosure.
Figure 12:
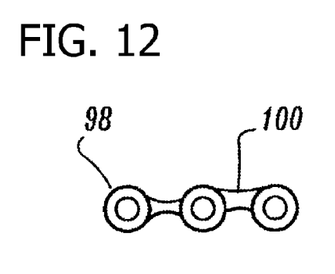
FIG. 12 is a front view of webbed tubing having an increased webbing volume according to an illustrative embodiment of the present.

Referring to FIGS. 11 and 12, certain embodiments are provided wherein the first plurality of fluid conduits 18 is a set of webbed tubing 98 having increased webbing volume 100 between at least one pair of adjacent conduits. At least one interference rib 94 is formed between at least one pair of adjacent fluid ports in the first plurality of fluid ports. The increased webbing volume 100 is aligned with the interference rib 94 if the set of webbed tubing 98 is improperly oriented with the first connector 12. The interference rib 94 thereby prevents attachment of improperly oriented fluid conduits to the first connector 12. Similarly, the second plurality of fluid conduits 22 can include an increased webbing volume configured to interfere with an interference rib between adjacent ports in the second connector 14 to prevent attachment of improperly oriented fluid conduits to the second connector 14.

Figure 13:
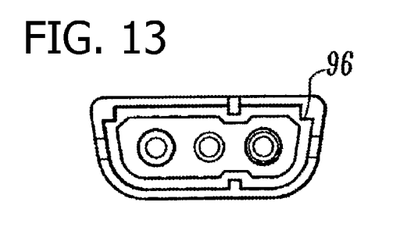
FIG. 13 is an end view of a first or second connector including an interference key according to an illustrative embodiment of the present disclosure.
Figure 14:
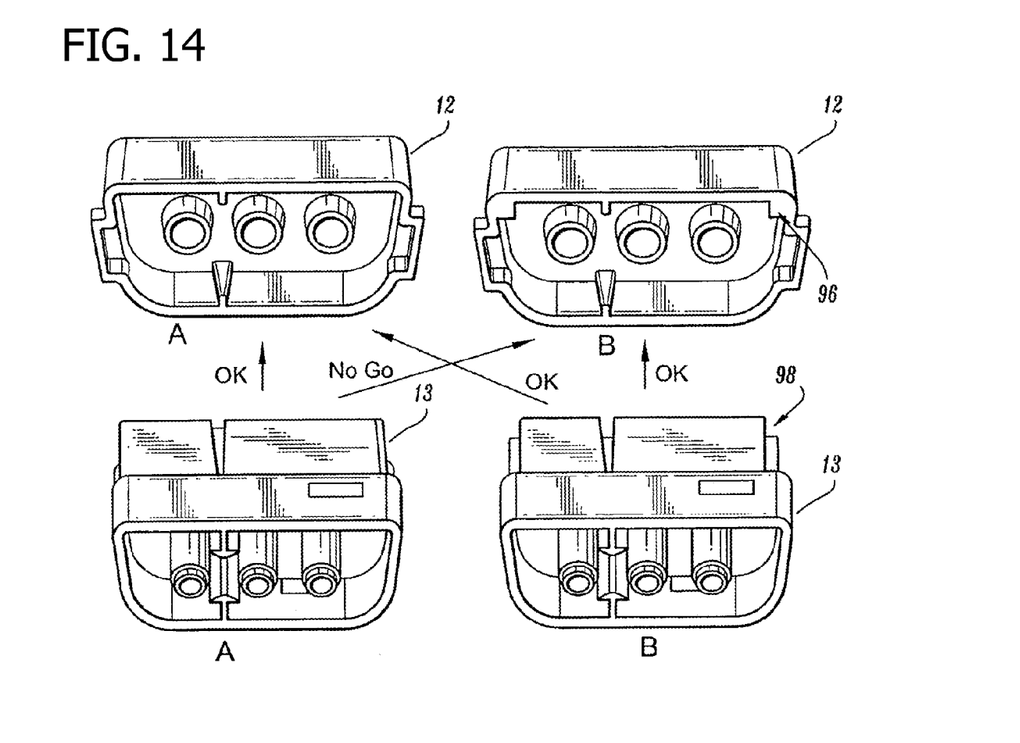
FIG. 14 is a schematic view of two embodiments of a first connector and two embodiments of a second connector.

Referring to FIG. 13, one embodiment includes a first connector 12 having an interference key 96 in the cavity 26 to prevent the first connector 12 from mating with legacy connector components. The second connector 14 includes a clearance space for the interference key 96. FIG. 14 schematically depicts the function of an interference key 96 to prevent connection of certain embodiments of a first connector 12 to certain embodiments of a second connector 13. For example, key slot 98 in second connector 13B provides clearance for interference key 96 in first connector 12B to facilitate mating one to the other. Second connector 13B can also be mated to certain first connectors such as 12A which do not include an interference key. Second connector 13A does not include a key slot and therefore can not be mated with first connector 12B. In at least one embodiment, second connector 13A is a legacy connector. In the illustrative embodiment, the interference key 96 in a non-compatible connector such as first connector 12B is used to prevent connection of the non-compatible connector to the legacy connector.

It will be understood that various modifications may be made to the embodiments disclosed herein. For example, the connector of the present disclosure may be used with various single and plural bladder compression sleeve devices including, for example, the compression sleeve described in U.S. patent application Ser. No. 10/784,323, filed on Feb. 23, 2004 and entitled Compression Apparatus, the entire contents of which is hereby incorporated by reference herein. Therefore, the above description should not be construed as limiting, but merely as exemplification of the various embodiments. Those skilled in the art will envision other modifications within the scope and spirit of the claims appended hereto.

What is claimed is:

1. A fluid connector apparatus adapted for use with a compression apparatus, the fluid connector apparatus comprising:

a pressurized fluid source;

a controller, the controller further comprising instructions providing a timed sequence of the pressurized fluid to a compression sleeve attached to a second connector;

a first connector, the fluid connector apparatus further having a first position and a second position, both positions allow for fluid flow therethrough a fluid orifice located at the first connector;

the second connector is releasably attached to the first connector, at a proximal end of the orifice of the first connector, wherein the fluid orifice further includes a valve disposed in the fluid orifice;

in the first position the valve is in a substantially open position by the second connector, the pressurized fluid source delivers a pressurized fluid through the valve to the compression sleeve in fluid communication with the fluid orifice; and in the second position the second connector is detached from the first connector, the valve advances in a proximal direction in the fluid orifice, the pressurized fluid source continues to deliver the fluid through the valve, when the valve substantially reduces but does not close the fluid orifice to fluid flow therethrough for approximating the pneumatic behavior of the detached compression sleeve at the second connector.

2. The fluid connector apparatus according to claim 1 wherein said first connector includes a cap portion disposed therein and said valve engages said cap portion for limiting the travel of the valve.

3. The fluid connector apparatus according to claim 1 wherein said second connector includes a locking arm extending therefrom such that said locking arm is adapted to releasably retain said first connector with said second connector.

4. The fluid connector apparatus according to claim 3 wherein said first connector includes a slot for engaging said locking arm.

5. The fluid connector apparatus according to claim 1, wherein said second connector includes an engagement portion extending therefrom and said valve is displaced by said engagement portion when said second connector is mated to said first connector.

6. The fluid connector apparatus according to claim 1, wherein the valve has a biasing member comprising at least one of the following: a spring, a plastic cantilever spring arm, and a elastometric material forming a gasket.

7. The fluid connector apparatus according to claim 6, wherein the valve is biased substantially open in the first position.

8. The fluid connector apparatus according to claim 1, wherein at least one of the orifice and the valve has a slot therein.

9. The fluid connector apparatus according to claim 1, wherein the valve further includes a plunger and a valve seat having at least one slot.

10. A method of operating the fluid compression apparatus of claim 1 to approximate the pneumatic behavior of the detached compression sleeve at the second connector comprising:

disconnecting the second connector from the first connector wherein the valve further comprises a slot therethrough at least at one of the orifice and the valve for fluid flow therethrough.

* * * * *